United States Patent
Shardt et al.

(10) Patent No.: US 11,007,500 B2
(45) Date of Patent: May 18, 2021

(54) GRADIENT INDUCED PARTICLE MOTION IN SUSPENSIONS

(71) Applicant: The Trustees of Princeton University, Princeton, NJ (US)

(72) Inventors: Orest Shardt, Princeton Jct., NJ (US); Sangwoo Shin, Princeton, NJ (US); Suin Shim, Princeton, NJ (US); Patrick B. Warren, Wirral (GB); Howard A. Stone, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 490 days.

(21) Appl. No.: 15/913,649

(22) Filed: Mar. 6, 2018

(65) Prior Publication Data

US 2018/0257054 A1 Sep. 13, 2018

Related U.S. Application Data

(63) Continuation-in-part of application No. PCT/US2017/049819, filed on Sep. 1, 2017.

(60) Provisional application No. 62/469,755, filed on Mar. 10, 2017.

(51) Int. Cl.
| | | |
|---|---|---|
| *B01J 13/00* | (2006.01) | |
| *G01N 33/00* | (2006.01) | |
| *G01N 15/06* | (2006.01) | |
| *B01D 65/08* | (2006.01) | |
| *G01N 1/40* | (2006.01) | |
| *B01D 61/14* | (2006.01) | |
| *G01N 15/10* | (2006.01) | |
| *B01D 61/00* | (2006.01) | |

(52) U.S. Cl.
CPC .......... *B01J 13/0039* (2013.01); *B01D 61/00* (2013.01); *B01D 61/14* (2013.01); *B01D 65/08* (2013.01); *G01N 1/4055* (2013.01); *G01N 15/06* (2013.01); *G01N 15/10* (2013.01); *G01N 33/0004* (2013.01); *B01D 61/145* (2013.01); *B01D 61/147* (2013.01); *B01D 2321/18* (2013.01); *G01N 1/4005* (2013.01)

(58) Field of Classification Search
None
See application file for complete search history.

(56) References Cited

U.S. PATENT DOCUMENTS

2008/0213593 A1* 9/2008 Bala Subramaniam ..................... B01F 13/0062
428/402.2

OTHER PUBLICATIONS

Shin et al., Size-dependent control of colloid transport via solute gradients in dead-end channels, 113 PNAS, 257, 257-261 (2016). (Year: 2016).*
Kar et al., Enhanced Transport into and out of Dead-End Pores, 9 ACS NANO, 746, 746-753 (2015). (Year: 2015).*
Anderson et al., Diffusiophoresis: Migration of Colloidal Particles in Gradients of Solute Concentration, Dept. of Chemical Engineering, Carnegie-Mellon University (1984). (Year: 1984).*
Abecassis et al., Boosting migration of large particles by solute constrasts, 7 Nature Materials, 785, 785-789 (2008). (Year: 2008).*
Ajdari et al., Giant Amplification of Interfacially Driven Transport by Hydrodynamic Slip: Diffusio-Osmosis and Beyond, 96 Phys. Rev. Let., 186102-1, 186102-1-186102-4 (2006). (Year: 2006).*
Ebel et al., Diffusiophoresis of Latex Particles in Electrolyte Gradients, 4 Langmuir, 396, 396-406 (1988). (Year: 1988).*
Prieve et al., Diffusiophoresis of a Rigid Sphere through a Viscous Electrolyte Solution, 2 J. Chem. Soc., Faraday Trans., 1287, 1287-1306 (1987) (Year: 1987).*

* cited by examiner

*Primary Examiner* — Krishnan S Menon
*Assistant Examiner* — Brad Gordon
(74) *Attorney, Agent, or Firm* — J. Clinton Wimbish; Nexsen Pruet, PLLC

(57) ABSTRACT

Methods of inducing or controlling particle motion in suspensions and colloids are described. In one aspect, a method of inducing particle motion in a suspension comprises contacting the suspension with a gas phase to establish at least one interface between the gas phase and continuous phase of the suspension. One or more gases of the gas phase are transferred across the interface to provide a solute gradient in the continuous phase, the solute gradient inducing motion of the suspended particles.

23 Claims, No Drawings

GRADIENT INDUCED PARTICLE MOTION IN SUSPENSIONS

RELATED APPLICATION DATA

The present application claims priority pursuant to 35 U.S.C. § 119(e) to U.S. Provisional Patent Application Ser. No. 62/469,755, filed Mar. 10, 2017 and to International Application PCT/US2017/049819, filed Sep. 1, 2017, both of which are hereby incorporated by reference in their entireties.

FIELD

The present invention relates suspensions and colloidal compositions and, in particular, to methods of inducing or affecting particle motion in suspensions and colloids.

BACKGROUND

Particle motion or transport in suspensions and colloids is important in many applications including drug delivery, disinfection and filtration. Several mechanisms exist to induce directed motion of colloidal particles, such as employment of one or more external forces. External forces can include electrostatic, dielectric, magnetic, acoustic, optical and/or inertial effects. Effective application of external forces can necessitate apparatus of complex architecture and design. Moreover, filtration of colloidal compositions often requires substantial amounts of energy and expensive apparatus comprising one or more membranes having pore size suitable for capture of ultrafine particles. Additionally, such filtration apparatus require routine maintenance to preclude membrane clogging or fouling.

SUMMARY

In view of these disadvantages, new methods of inducing or controlling particle motion in suspensions and colloids are needed. In one aspect, a method of inducing or affecting particle motion in a suspension comprises contacting the suspension with a gas phase to establish at least one interface between the gas phase and continuous phase of the suspension. One or more gases of the gas phase are transferred across the interface to provide a solute gradient in the continuous phase, the solute gradient inducing or affecting motion of the suspended particles. In some embodiments, for example, the solute gradient induces the suspended particles to move toward the interface of the gas phase and continuous phase. In other embodiments, the solute gradient induces the suspended particles to move away from the interface.

In another aspect, analytical methods are described. In some embodiments, an analytical method comprises providing a suspension in a chamber, the suspension comprising analyte particles suspended in a continuous phase. The suspension is contacted with a gas phase to establish at least one interface between the gas phase and continuous phase. One or more gases of the gas phase are transferred across the interface to provide a solute gradient in the continuous phase, the solute gradient concentrating the analyte particles in a region of the chamber. The concentrated analyte particles can subsequently be detected and/or one or more properties of the analyte particles can be determined. In some embodiments, for example, analyte particles are present in the suspension at such low concentration that the particles cannot be readily detected. However, sufficient concentration of the analyte particles induced by the solute gradient can render the particles detectable.

In another aspect, methods of detecting soluble gases are described. A method of detecting a soluble gas comprises providing a suspension in a chamber and contacting the suspension with a gas sample to establish at least one interface between the gas sample and continuous phase of the suspension. Particle motion is detected in response to a solute gradient produced by dissolution of one or more gases from the sample after crossing the interface.

In a further aspect, methods of inhibiting fouling of surfaces in contact with fluids are described. A method of inhibiting fouling of a surface in contact with a fluid comprises contacting the fluid with a gas phase to establish at least one gas-fluid interface. One or more gases of the gas phase are transferred across the interface to provide a solute gradient in the fluid, the solute gradient inducing particle motion in the fluid away from the surface. In some embodiments, for example, the gas-fluid interface is adjacent to the surface, and the solute gradient repels the particles from the surface. In other embodiments, the gas-fluid interface is spaced apart from the surface, and the solute gradient attracts particles, thereby directing particle motion away from the surface.

These and other embodiments are described in further detail in the detailed description which follows.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

I. Gradient Induced Particle Motion

In one aspect, a method of inducing or affecting particle motion in a suspension comprises contacting the suspension with a gas phase to establish at least one interface between the gas phase and continuous phase of the suspension. One or more gases of the gas phase are transferred across the interface to provide a solute gradient in the continuous phase, the solute gradient inducing or affecting motion of the suspended particles. In some embodiments, for example, the solute gradient induces the suspended particles to move toward the interface of the gas phase and continuous phase. In other embodiments, the solute gradient induces the suspended particles to move away from the interface.

Turning now to specific components, the suspension continuous phase can comprise any species not inconsistent with the objectives of the present invention. In some embodiments, the continuous phase exhibits protic character. For example, the continuous phase can be water or aqueous-based. When aqueous-based, the continuous phase may comprise other protic species including carboxylic acids, alcohols, amines or mixtures thereof. Aqueous-based continuous phase may also include one or more polar aprotic species such as N-methylpyrrolidone, acrylonitrile, acetone, tetrahydrofuran (THF), ethyl acetate, acetone, dimethylformamide (DMF), acetonitrile or dimethyl sulfoxide (DMSO) or various mixtures thereof. In some embodiments, the continuous phase can comprise one or more species operable to react with gas for ion generation. As described further herein, ions generated by reaction of gas with the continuous phase can produce an ion concentration gradient for inducing particle motion in the suspension. Species of the continuous phase interfering with or precluding the formation of an ion concentration gradient upon introduction of a gas into or removal of a gas from the continuous phase should generally be avoided, but may be present in low concentrations.

However, species can be added to the continuous phase to affect one or more properties of the ion concentration gradient produced by dissolution of gas in the continuous phase. In some embodiments, an additive to the continuous phase can enhance or retard the strength/diffusion potential of the ion concentration gradient. In other embodiments, an additive can increase or diminish duration of the ion concentration gradient. Additives can comprise various ionic species such as salts and/or acids. Additives can also comprise protic and polar aprotic species described above. Compositional identity and/or amount of additive can be selected according to several considerations, including but not limited to, the specific identities of the continuous phase and gas phase, particle composition and surface charge, as well as the desired effect on the ion concentration gradient. In some embodiments, additive(s) can be added to the continuous phase to assist in selective separation of suspended particles.

In addition to the foregoing polar liquids, the continuous phase may comprise one or more hydrophobic or non-polar liquids, in some embodiments. Gases dissolved in a non-polar continuous phase may produce compositional gradients in the continuous phase operable for affecting or inducing motion of the suspended particles. Accordingly, solute gradients affecting particle motion in the suspension include gradients of dissolved gas molecules in addition to ionic gradients formed by reaction of one or more gases with the continuous phase. Gradients of dissolved gas molecules can also be present in polar or hydrophilic continuous phases.

In further embodiments, the continuous phase may be a gas as opposed to a liquid. For example, a gaseous continuous phase may comprise water vapor or a mixture of water vapor with other gases. A gaseous continuous phase, in some embodiments, is operable to react with one or more gases to provide ion concentration gradients for affecting or inducing movement of particles suspended in the continuous phase. In this way, particle concentration and/or separation techniques based on induced particle movement are not limited to liquid phase applications.

As described herein, the suspension is contacted with a gas phase to establish at least one interface between the gas phase and continuous phase of the suspension. The gas phase comprises at least one gas that is soluble in the continuous phase. In some embodiments, the gas phase can comprise a plurality of gases soluble in the continuous phase. The gas phase can contact the continuous phase in any desired manner to establish an interface between the gas phase and continuous phase. In some embodiments, the gas phase is flowed over a surface of the continuous phase. In such embodiments, a continuous or uninterrupted interface is formed between the gas phase and continuous phase. Alternatively, a discontinuous interface can be formed between the gas phase and the continuous phase. For example, a porous membrane can be positioned between the gas phase and continuous phase. Pores of the membrane passing one or more gases of the gas phase into or out of the continuous phase establish an interrupted or discontinuous interface. In further embodiments, the gas phase can be bubbled or injected into the continuous phase. Bubbling or injecting can create multiple independent interfaces between the gas phase and continuous phase.

One or more gases of the gas phase are transferred across the interface to provide solute gradient(s) affecting motion of the suspended particles. The solute gradient can be compositional in nature wherein particle motion is affected by amount(s) of gas dissolved in the continuous phase. In other embodiments, the solute gradient can be an ion concentration gradient formed by reaction of the gas with the continuous phase to provide ionic species. The ionic species can exhibit large differences in their diffusivities in the continuous phase, thereby providing a large diffusion potential. Solubility of one or more gases in the continuous phase will necessarily depend on compositional identity of the continuous phase. In some embodiments wherein the continuous phase is water or is aqueous-based, the gas phase can comprise one or more gases selected from the group consisting of $H_2S$, $CO_2$, HCN, HCl, HBr, HF, HI, $Cl_2$, $N_2O_4$, $NO_2$, $SO_2$, $SO_3$ and $NH_3$. In other embodiments, volatile organic acids can be employed as a gas phase in conjunction with a water or aqueous-based continuous phase. Suitable volatile organic acids include formic acid and ethanoic acid.

Solubility of one or more gases in the continuous phase can be controlled by several considerations including, but not limited to, the specific identities of the gas and continuous phase, gas pressure, and temperature of the continuous phase. For example, reaction rates of gas species with the continuous phase can be enhanced by higher temperatures, while gas solubility is generally increased by lower temperatures.

In some embodiments, solute gradients, including ion concentration gradients, affecting or inducing particle motion are formed via stripping one or more gas species from the continuous phase. In such embodiments, the continuous phase is initially saturated with the gas to be stripped. Once saturated, the gas can be stripped by exposing the suspension to an atmosphere lacking the gas. Alternatively, or in addition, a stripping gas can be bubbled or injected into the continuous phase for removal of the desired gas species.

In some embodiments, the solute gradient induces the suspended particles to move toward the interface of the gas phase and continuous phase. In other embodiments, the solute gradient induces the suspended particles to move away from the interface. Movement of the particles in response to solute gradients can concentrate the particles in a region of a conduit or container. Concentration of the particles can enable easy separation or collection of the particles. Accordingly, methods described herein can be used for filtration applications. Advantageously, the methods do not require a filtration membrane, thereby significantly lowering power requirements and costs of routine maintenance. In some embodiments, the particles are driven towards bubbles in the suspension, wherein the particles attach to the bubbles for subsequent removal or collection.

Particles suspended in the continuous phase and moved according to methods described herein can have any desired composition. In some embodiments, the particles are inorganic compositions, such as metals, alloys, minerals, fine rock and/or semiconductor particles. The suspended particles may also be organic in nature including, but not limited to, polymeric particles. In other embodiments, the suspended particles are biological including bacteria, viruses, nucleic acids, proteins, lipids or mixtures thereof. The suspended particles can also have complex architectures, such as core/shell constructs. The suspended particles, for example, can be micelles and related surfactant structures. Moreover, the suspended particles are liquid particles, in some embodiments.

The suspended particles, solid or liquid, can exhibit surface charges for interacting with ionic concentration gradients formed by dissolution and reaction of one or more gases with the continuous phase. The suspended particles can have any desired size. In some embodiments, the suspended particles have an average size less than 1 µm. Average size of the suspended particles can be selected from Table I, in some embodiments.

TABLE I

Average Size of Suspended Particles

| ≤500 nm |
| 1-100 nm |
| 10-200 nm |
| 50-150 nm |

As set forth in Table I, the particles can be sufficiently small to provide colloidal compositions. In other embodiments, average size of the suspended particles can be 1 µm or greater.

II. Analytical Methods

In another aspect, analytical methods are described. In some embodiments, an analytical method comprises providing a suspension in a chamber, the suspension comprising analyte particles suspended in a continuous phase. The suspension is contacted with a gas phase to establish at least one interface between the gas phase and continuous phase. One or more gases of the gas phase are transferred across the interface to provide a solute gradient in the continuous phase, the solute gradient concentrating the analyte particles in a region of the chamber. The concentrated analyte particles can subsequently be detected and/or one or more properties of the analyte particles can be determined.

In some embodiments, for example, analyte particles are present in the suspension at such low concentration that the particles cannot be readily detected. Analyte particles, for example, can be present in the suspension at nanomolar, picomolar or femtomolar levels prior to solute gradient formation. Notably, sufficient concentration of the analyte particles induced by the solute gradient can render the particles detectable. In some embodiments, spectroscopic measurements and data can be taken from the concentration of analyte particles. The spectroscopic data may be sufficient to identify compositional parameters for affirmative identification of the analyte. Moreover, analyte particles can be sufficiently small to provide colloidal compositions for analysis. Analyte particles may have an average size selected from Table I, in some embodiments.

Analyte particles can have any compositional parameters consistent with methods described herein. Analyte particles, for example, can comprise inorganic compositions, polymeric compositions and/or biological compositions. Analyte particles may be solid or liquid and can exhibit surface charges. Moreover, solute gradients, including ion concentration gradients, for inducing motion of the analyte particles can be produced in a manner consistent with that described in Section I herein.

III. Soluble Gas Detection

In another aspect, methods of detecting soluble gases are described. A method of detecting a soluble gas comprises providing a suspension in a chamber and contacting the suspension with a gas sample to establish at least one interface between the gas sample and continuous phase of the suspension. Particle motion is detected in response to a solute gradient produced by dissolution of one or more gases from the sample after crossing the interface. Formation and properties of the solute gradient, including ion concentration gradient(s), are described in detail in Section I herein.

Compositional parameters of the suspension can be selected according to properties of the gas or gases to be detected. For example, for gases soluble in polar or hydrophilic media, the continuous phase can be water or aqueous-based solution as described in Section I herein. In some embodiments, the continuous phase can also be selected to react with the gas to provide an ion concentration gradient inducing particle motion. The suspended particles may exhibit surface charge to enhance particle motion in response to a solute gradient, including an ion concentration gradient. Careful control of suspension or colloid compositional parameters can selectively detect the presence of one or more gases in a gas sample, thereby enabling monitoring of various atmospheric or environmental species. In some embodiments, for example, harmful gases such as $H_2S$, $SO_2$ and/or $SO_3$ can be detected and monitored according to the present methods. Degree of particle motion in response to the presence of a gas species may be correlated to levels of the gas species in the atmosphere or local environment. Additionally, such monitoring can be continuous or periodic.

IV. Surface Fouling Inhibition

In a further aspect, methods of inhibiting fouling of surfaces in contact with fluids are described. A method of inhibiting fouling of a surface in contact with a fluid comprises contacting the fluid with a gas phase to establish at least one gas-fluid interface. One or more gases of the gas phase are transferred across the interface to provide a solute gradient in the fluid, the solute gradient inducing particle motion in the fluid away from the surface. In some embodiments, for example, the gas-fluid interface is adjacent to the surface, and the solute gradient repels the particles from the surface. In other embodiments, the gas-fluid interface is spaced apart from the surface, and the solute gradient attracts particles, thereby directing particle motion away from the surface. Formation and properties of the solute gradient, including ion concentration gradient(s), are described in detail in Section I herein.

In some embodiments, the surface in contact with the fluid is porous. The porous surface, for example, can be a filter or a membrane. Filters or membranes can have any desired construction and/or properties. In some embodiments, the filter or membrane is part of a microfiltration or ultrafiltration apparatus. The present method can extend filter or membrane lifetime and/or extend operating periods between required maintenance, such as filter or membrane cleaning or replacement.

As described herein, the gas phase can react with the fluid to provide an ion concentration gradient. One or more gases can be selected such that ions forming the concentration gradient do not foul or interfere with the function of the surface contacting the fluid. In some embodiments, the fluid is a liquid. In other embodiments, the fluid is a gas. The fluid can be in stationary contact with the surface. Alternatively, the fluid can be flowing across or though the surface, when porous. When stationary, the fluid can be periodically contacted with the gas phase to establish or maintain the solute gradient. When flowing, the fluid can be continuously contacted with the gas phase to establish or maintain the solute gradient.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of inducing or affecting particle motion in a suspension comprising:
   contacting the suspension with a gas phase to establish at least one interface between the gas phase and suspension continuous phase;
   transferring one or more gases of the gas phase across the interface to provide a solute gradient in the continuous phase, the solute gradient inducing or affecting motion of the suspended particles.

2. The method of claim 1, wherein the solute gradient induces the suspended particles to move toward the interface.

3. The method of claim 1, wherein the solute gradient induces the suspended particles to move away from the interface.

4. The method of claim 1, wherein the one or more gases are dissolved in the continuous phase.

5. The method of claim 4, wherein the one or more gases react with the continuous phase to provide an ion concentration gradient.

6. The method of claim 1, wherein the one or more gases interact with an additive in the continuous phase to provide the solute gradient.

7. The method of claim 1, wherein the one or more gases are transferred across the interface out of the continuous phase.

8. The method of claim 1, wherein the suspended particles are dispersed throughout the continuous phase prior to contact of the suspension with the gas phase.

9. The method of claim 1, wherein the suspension is a colloid.

10. The method of claim 1, wherein the continuous phase is water or aqueous-based.

11. The method of claim 1, wherein the continuous phase is a gas.

12. The method of claim 1, wherein the suspended particles exhibit surface charge.

13. The method of claim 1, wherein the suspended particles are concentrated by the solute gradient.

14. The method of claim 13 further comprising isolating the suspended particles from the suspension.

15. The method of claim 1, wherein a plurality of gases are transferred across the interface.

16. The method of claim 1, wherein the suspended particles comprise biological species selected from the group consisting of bacteria, viruses, nucleic acids, proteins, lipids and mixtures thereof.

17. An analytical method comprising:
   disposing a suspension in a chamber, the suspension comprising analyte particles suspended in a continuous phase;
   contacting the suspension with a gas phase to establish at least one interface between the gas phase and continuous phase;
   transferring one or more gases of the gas phase across the interface to provide a solute gradient in the continuous phase, the solute gradient concentrating the analyte particles in a region of the chamber; and
   detecting the concentrated analyte particles and/or determining one or more properties of the concentrated analyte particles.

18. A method of inhibiting fouling of a surface in contact with a fluid comprising:
   contacting the fluid with a gas phase to establish at least one gas-fluid interface;
   transferring one or more gases of the gas phase across the interface to provide a solute gradient in the fluid, the solute gradient inducing particle motion in the fluid away from the surface.

19. The method of claim 18, wherein the gas-fluid interface is adjacent to the surface, and the solute gradient repels particles from the surface.

20. The method of claim 18, wherein the gas-fluid interface is spaced apart from the surface, and the solute gradient attracts particles, thereby directing particle motion away from the surface.

21. The method of claim 18, wherein the surface is porous.

22. The method of claim 21, wherein the surface is a filter or membrane.

23. A method of detecting a soluble gas comprising:
   providing a suspension in a chamber, the suspension comprising particles suspended in a continuous phase;
   contacting the suspension with a gas sample to establish at least one interface between the gas sample and the continuous phase; and
   detecting particle motion in the continuous phase in response to a solute gradient produced by dissolution of one or more gases from the sample after crossing the interface.

* * * * *